US011236297B2

United States Patent
Fujimoto et al.

(10) Patent No.: US 11,236,297 B2
(45) Date of Patent: Feb. 1, 2022

(54) METHOD OF PRODUCING CELL CULTURE CHIP

(71) Applicant: TOKYO OHKA KOGYO CO., LTD., Kawasaki (JP)

(72) Inventors: Takashi Fujimoto, Kawasaki (JP); Emi Maeno, Kawasaki (JP); Yasushi Fujii, Kawasaki (JP); Hirotsugu Kumazawa, Kawasaki (JP)

(73) Assignee: Tokyo Ohka Kogyo Co., Ltd., Kawasaki (JP)

( * ) Notice: Subject to any disclaimer, the term of this patent is extended or adjusted under 35 U.S.C. 154(b) by 0 days.

(21) Appl. No.: 17/152,269

(22) Filed: Jan. 19, 2021

(65) Prior Publication Data

US 2021/0222106 A1 Jul. 22, 2021

(30) Foreign Application Priority Data

Jan. 22, 2020 (JP) .............................. JP2020-008704

(51) Int. Cl.
*C12M 3/06* (2006.01)
*B32B 37/12* (2006.01)

(52) U.S. Cl.
CPC ............ *C12M 23/16* (2013.01); *B32B 37/12* (2013.01); *B32B 2037/1253* (2013.01); *B32B 2310/0831* (2013.01)

(58) Field of Classification Search
CPC ....... C12M 23/16; C12M 33/00; B32B 37/12; B32B 2037/1253; B32B 2310/0831; B29C 64/124; B33Y 80/00; B33Y 10/00; G03F 7/027; G03F 7/0037; G03F 7/2051
See application file for complete search history.

(56) References Cited

U.S. PATENT DOCUMENTS 6,752,966 B1 * 6/2004 Chazan ............. B01L 3/502707
422/500
2004/0253545 A1 12/2004 David
2011/0207220 A1 8/2011 Okano et al.
(Continued)

FOREIGN PATENT DOCUMENTS

EP 3342852 A2 * 7/2018 ............ C12M 23/22
EP 3342852 A2 7/2018
(Continued)

OTHER PUBLICATIONS

Search Report in European Patent Application No. 21152426.9, dated Jun. 15, 2021.

*Primary Examiner* — Vishal I Patel
(74) *Attorney, Agent, or Firm* — Knobbe Martens Olson & Bear LLP

(57) ABSTRACT

A method of producing a cell culture chip, in which a first adhesive is film-formed on a first substrate having transparency such that a first adhesive layer and a recessed portion on which one or more cell culture flow paths are formed face each other, and a second adhesive is film-formed on the first substrate such that a second adhesive layer and a flat portion around the recessed portion face each other, thereby obtaining a cell culture flow path substrate, the first adhesive containing a polyester-based resin having a glass transition temperature of 5° C. or higher, and the second adhesive containing a polyester-based resin having a glass transition temperature of lower than 5° C.

5 Claims, 4 Drawing Sheets

(56) References Cited

U.S. PATENT DOCUMENTS

| | | | |
|---|---|---|---|
| 2012/0009665 A1* | 1/2012 | Lin | B32B 38/145 |
| | | | 435/287.2 |
| 2012/0129208 A1* | 5/2012 | Khine | B01L 3/5085 |
| | | | 435/29 |
| 2013/0037207 A1* | 2/2013 | Yamamoto | B29C 65/8215 |
| | | | 156/273.3 |
| 2013/0096029 A1 | 4/2013 | Sia et al. | |
| 2014/0048980 A1* | 2/2014 | Crump | B29C 64/106 |
| | | | 264/401 |
| 2015/0174573 A1 | 6/2015 | Esch | |
| 2018/0179481 A1 | 6/2018 | Fujimoto et al. | |

FOREIGN PATENT DOCUMENTS

| | | | | |
|---|---|---|---|---|
| JP | 2010-112730 A | 5/2010 | | |
| JP | 2015-535728 A | 12/2015 | | |
| JP | 2018-102236 A | 7/2018 | | |
| WO | WO-2009042671 A1 * | 4/2009 | | B81C 1/00119 |
| WO | WO 2014/046621 A1 | 3/2014 | | |
| WO | WO 2016/164861 A1 | 10/2016 | | |

\* cited by examiner

[OPERATION (a1)]

[OPERATION (a2)]

[OPERATION (a3)]

[OPERATION (a4)]

[STEP B]

[STEP C]

180# METHOD OF PRODUCING CELL CULTURE CHIP

BACKGROUND OF THE INVENTION

Field of the Invention

The present invention relates to a method of producing a cell culture chip.

Priority is claimed on Japanese Patent Application No. 2020-008704, filed on Jan. 22, 2020, the content of which is incorporated herein by reference.

Description of Related Art

A frequently occurring problem of monolayer culture which has been used for cell assays of the related art is that the environment surrounding cells is greatly different from that in a living body, and many of the functions exhibited in the body are lost in the cultured cells. It is expected that the above-described problem is solved by recent advances in microfabrication technology and 3D culture technology so that the throughput and reliability of cell assays are improved at the same time. In particular, the concept of organ-on-a-chip, which handles cell culture chips provided with a microfluidic device that reproduces a physiological three-dimensional culture environment in vitro as one organ, has spread, and the research in consideration of the applications for drug development has been widely developed worldwide. Further, the concept of body-on-a-chip, which aims to reproduce individual responses by connecting a plurality of organ models reconstructed in vitro with microflow paths and the like, has been proposed and has been attracting attention rapidly.

In the related art, the cell culture chips described above are produced by a soft lithography method (see, for example, Published Japanese Translation No. 2015-535728 of the PCT International Publication) or an injection molding method (see, for example, Japanese Unexamined Patent Application, First Publication No. 2010-112730).

However, in a case of the soft lithography method in the methods of producing a cell culture chip of the related art, a fine flow path structure can be produced, but the method is suitable for small-quantity production and not suitable for mass production.

On the contrary, the injection molding method is suitable for mass production, but it is costly to produce a mold having a fine flow path structure.

Further, the cell culture chip is required to have a function of realizing cell culture, a function of realizing observation the inside thereof, and the like.

Meanwhile, a method of producing a cell culture chip including a microflow path structure having a hollow structure, which is obtained by thermocompression-bonding a substrate on which a cell culture flow path is formed to a top plate that blocks the cell culture flow path through a specific adhesive layer, has been suggested (see, for example, Japanese Unexamined Patent Application, First Publication No. 2018-102236). According to this production method, a fine flow path structure can be produced, and mass production can be made at a low cost. In addition, a cell culture chip having a function suitable for cell culture can be produced.

SUMMARY OF THE INVENTION

According to the method of producing a cell culture chip described in Japanese Unexamined Patent Application, First Publication No. 2018-102236, in a case where the substrate and the top plate are bonded to each other, a fine flow path structure can be stably formed without blocking the flow path in the flow direction.

However, in the cell culture chip produced by the production method described in Japanese Unexamined Patent Application, First Publication No. 2018-102236, there is a problem in that liquid leakage from the flow path may easily occur while a culture solution at approximately 37° C. is allowed to flow in a case where the chip has a complicated flow path structure.

The present invention has been made in consideration of the above-described circumstances and provides a method of producing a cell culture chip, which enables stable production of a fine flow path structure and in which liquid leakage from the flow path is suppressed.

According to an aspect of the present invention, there is provided a method of producing a cell culture chip including a microflow path structure in which a cell culture flow path substrate on which a cell culture flow path is formed is bonded to a cell culture flow path top plate through an adhesive layer, the method including: a step A of obtaining a cell culture flow path substrate including a recessed portion on which one or more cell culture flow paths are formed and a flat portion around the recessed portion, the flat portion being a portion which is bonded to the cell culture flow path top plate; a step B of selectively disposing a first adhesive layer and a second adhesive layer on a first substrate having transparency to obtain a cell culture flow path top plate; and a step C of thermocompression-bonding the cell culture flow path substrate to the cell culture flow path top plate to obtain a microflow path structure having a hollow structure; in which in the step B, a first adhesive is film-formed on the first substrate such that the first adhesive layer and the recessed portion face each other, a second adhesive is film-formed on the first substrate such that the second adhesive layer and the flat portion face each other, the first adhesive contains a polyester-based resin having a glass transition temperature of 5° C. or higher, and the second adhesive contains a polyester-based resin having a glass transition temperature of lower than 5° C.

According to the present invention, it is possible to provide a method of producing a cell culture chip, which enables stable production of a fine flow path structure and in which liquid leakage from the flow path is suppressed.

Figure 1:
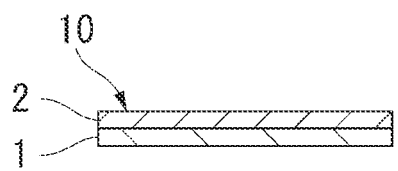
FIG. 1 is a cross-sectional view schematically illustrating a configuration in a step A for explaining an embodiment of a method of producing a cell culture chip.
Figure 1:
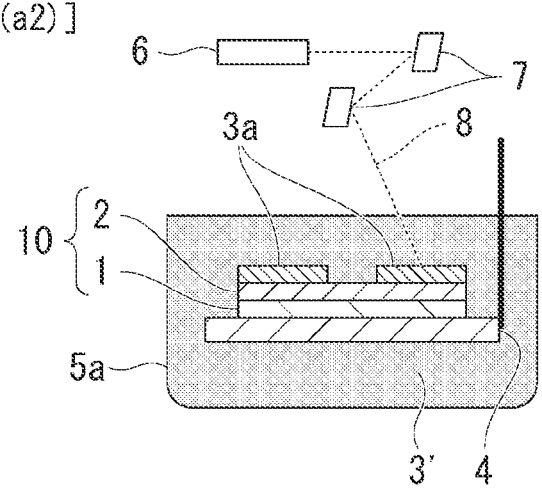
Figure 1:
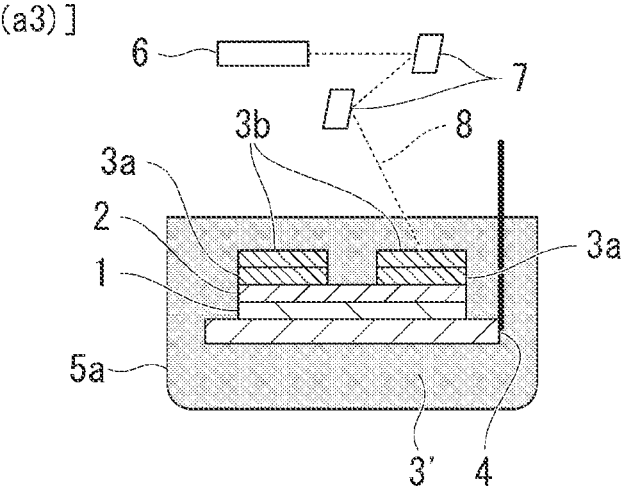
Figure 1:
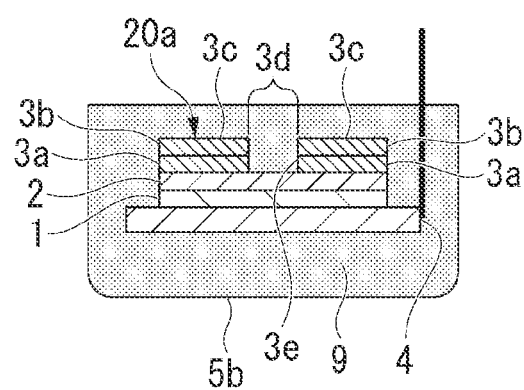

DETAILED DESCRIPTION OF THE INVENTION (Method of Producing Cell Culture Chip)

An embodiment of the present invention relates to a method of producing a cell culture chip including a microflow path structure in which a cell culture flow path substrate on which a cell culture flow path is formed is bonded to a cell culture flow path top plate through an adhesive layer.

The method of producing a cell culture chip according to the embodiment includes the following steps A, B, and C.

The step A is a step of obtaining a cell culture flow path substrate including a recessed portion on which one or more cell culture flow paths are formed and a flat portion around the recessed portion, which is a portion bonded to the cell culture flow path top plate.

The step B is a step of selectively disposing a first adhesive layer and a second adhesive layer on a first substrate having transparency to obtain a cell culture flow path top plate.

The step C is a step of thermocompression-bonding the cell culture flow path substrate to the cell culture flow path top plate through the first adhesive layer and the second adhesive layer which have been selectively disposed to obtain a microflow path structure having a hollow structure.

First Embodiment

As the method of producing a cell culture chip, a method in which a 3D printer is applied to a shaping method may be exemplified. Hereinafter, as the method of producing a cell culture chip according to the embodiment, a production method including the above-described steps A, B, and C, in which the above-described step A includes the following operations (a1) to (a4) will be described.

The operation (a1) is an operation of forming a photosensitive adhesive layer by coating the substrate having transparency with a photosensitive adhesive to obtain a 3D printing substrate.

The operation (a2) is an operation of selectively irradiating a photosensitive shaping material layer obtained by film-forming a photosensitive shaping material on the 3D printing substrate with ultraviolet rays to selectively cure the photosensitive shaping material layer.

The operation (a3) is an operation of further film-forming a photosensitive shaping material, allowing a photosensitive shaping material layer to be layered on the selectively cured photosensitive shaping material layer, and selectively irradiating the layered photosensitive shaping material layer with ultraviolet rays to selectively cure the layered photosensitive shaping material layer.

The operation (a4) is an operation of repeatedly performing the operation (a3) a plurality of times and subsequently developing an uncured portion, thereby obtaining a cell culture flow path substrate having the recessed portion and the flat portion.

<<Substrate Having Transparency>>

From the viewpoint of observing cultured cells using a phase contrast microscope, a substrate having transparency is used as the 3D printing substrate in the present embodiment. Further, in order to enhance the transparency, it is preferable that the substrate does not contain a filler (antiblocking agent).

As the material of the substrate having transparency, a transparent low autofluorescent substance is preferable. Preferred examples of the transparent low autofluorescent substance include glass, polyethylene terephthalate, polycarbonate, a cycloolefin polymer, polydimethylsiloxane, polystyrene, and polyacrylate (an acrylic resin).

The substrate having transparency may include a lubricative layer containing a lubricant component on at least one surface thereof. Further, a binder resin component may be blended into the lubricative layer.

The lubricant component is not particularly limited, and examples thereof include paraffin wax, microwax, polypropylene wax, polyethylene wax, ethylene-acrylic wax, stearic acid, behenic acid, 12-hydroxystearic acid, stearic acid amide, oleic acid amide, erucic acid amide, methylene bisstearic acid amide, ethylene bisstearic acid amide, ethylene bisoleic acid amide, butyl stearate, stearic acid monoglyceride, pentaerythritol tetrastearate, hydrogenated castor oil, stearyl stearate, siloxane, a higher alcohol-based polymer, stearyl alcohol, calcium stearate, zinc stearate, magnesium stearate, lead stearate, a silicone (dimethylsiloxane)-based low-molecular-weight substance (oil), and a silicone (dimethylsiloxane)-based resin. The lubricant component may be used alone or in combination of two or more kinds thereof.

Further, examples of the binder resin component to be blended in the lubricative layer includes various resins such as polyester-based resins, polyamide-based resins, polyurethane-based resins, epoxy-based resins, phenolic resins, acrylic resins, polyvinyl acetate resins, cellulose-based resins, styrene-based resins, and copolymer resins thereof. Among these, from the viewpoint of exhibiting an excellent lubricating property by combining the above-described lubricant component with the binder resin component, a styrene-acrylic copolymer resin is preferable as the binder resin component.

Further, in the present specification, the term "silicone-based" indicates organosiloxanes. The properties thereof may be oily, rubbery, and resinous and are referred to as silicone oil, silicone rubber, and a silicone resin, respectively. Since all of these have a water-repellent function, a lubrication function, a mold release function, and the like, in a case where the organosiloxanes are contained in the outermost layer portion of a film, the friction of the surface is effectively decreased.

<<Photosensitive Adhesive>>

It is preferable that the photosensitive adhesive has developer resistance. Since the photosensitive adhesive has developer resistance, the adhesiveness can be maintained without elution of the photosensitive adhesive even in a case of a development treatment in the subsequent operation (a4). Further, it is preferable that the photosensitive adhesive has adhesiveness to the above-described substrate having transparency, adhesiveness to the cell culture flow path substrate formed in the subsequent operations (a2) to (a4), transparency, low self-luminescence, and low cytotoxicity.

Photopolymerizable Compound

The photosensitive adhesive contains a photopolymerizable compound in an amount of preferably 30% by mass to 70% by mass and more preferably 40% by mass to 60% by mass with respect to the total mass (100% by mass) of the photosensitive adhesive.

The material of the photosensitive adhesive can be selected from various photopolymerizable compounds which have been used in photosensitive adhesives in the related art. From the viewpoints of the storage stability and the like of the photosensitive adhesive, a compound having an ethylenically unsaturated bond is preferable as the photopolymerizable compound.

Examples of the photopolymerizable functional group contained in the compound having an ethylenically unsaturated bond include a (meth)acryloyl group, a vinyl group, and an allyl group. As the compound having an ethylenically unsaturated bond, for example, a monofunctional, bifunctional, or trifunctional or higher polyfunctional (meth)acrylate compound, (meth)acrylamide compound, vinyl compound, or allyl compound can be used. These compounds having an ethylenically unsaturated bond can be used alone or in combination of two or more kinds thereof.

Examples of the compound having a monofunctional ethylenically unsaturated bond include (meth)acrylic acid esters, (meth)acrylamides, allyl compounds, vinyl ethers, vinyl esters, and styrenes.

Examples of the (meth)acrylic acid esters include methyl (meth)acrylate, ethyl (meth)acrylate, propyl (meth)acrylate, amyl (meth)acrylate, t-octyl (meth)acrylate, chloroethyl (meth)acrylate, 2,2-dimethylhydroxypropyl (meth)acrylate, 2-hydroxyethyl (meth)acrylate, trimethylolpropane mono (meth)acrylate, benzyl (meth)acrylate, furfuryl (meth)acrylate, phenyl (meth)acrylate, (meth)acrylate of an EO adduct of phenol, (meth)acrylate of a PO adduct of phenol, (meth)acrylate of an EO/PO coadduct of phenol, ethylene glycol mono(meth)acrylate, diethylene glycol mono(meth)acrylate, triethylene glycol mono(meth)acrylate, polyethylene glycol mono(meth)acrylate, 2-methoxyethyl (meth)acrylate, diethylene glycol monomethyl ether mono(meth)acrylate, triethylene glycol monomethyl ether mono(meth)acrylate, polyethylene glycol monoethyl ether mono(meth)acrylate, propylene glycol mono(meth)acrylate, dipropylene glycol mono(meth)acrylate, tripropylene glycol mono(meth)acrylate, polypropylene glycol mono(meth)acrylate, propylene glycol monomethyl ether mono(meth)acrylate, dipropylene glycol monomethyl ether mono(meth)acrylate, tripropylene glycol monomethyl ether mono(meth)acrylate, polypropylene glycol monomethyl ether mono(meth)acrylate, mono (meth)acrylate of an EO/PO copolymer, monomethyl ether mono(meth)acrylate of an EO/PO copolymer, and amine-modified polyether acrylate.

Further, in the present specification, the term "EO-modified" indicates a compound having a (poly)oxyethylene chain. The term "PO-modified" indicates a compound having a (poly)oxypropylene chain. The term "EO/PO-modified" indicates a compound having both a (poly)oxyethylene chain and a (poly)oxypropylene chain.

Examples of the (meth)acrylamides include (meth)acrylamide, N-alkyl (meth)acrylamide, N-aryl (meth)acrylamide, N,N-dialkyl (meth)acrylamide, N,N-aryl (meth)acrylamide, N-methyl-N-phenyl (meth)acrylamide, N-hydroxyethyl-N-methyl (meth)acrylamide.

Examples of the allyl compound include allyl esters such as allyl acetate, allyl caproate, allyl caprylate, allyl laurate, allyl palmitate, allyl stearate, allyl benzoate, allyl acetoacetate, and allyl lactate; and allyloxyethanol.

Examples of the vinyl ethers include alkyl vinyl ether such as hexyl vinyl ether, octyl vinyl ether, decyl vinyl ether, ethyl hexyl vinyl ether, methoxyethyl vinyl ether, ethoxyethyl vinyl ether, chloroethyl vinyl ether, 1-methyl-2,2-dimethylpropyl vinyl ether, 2-ethylbutyl vinyl ether, hydroxyethyl vinyl ether, diethylene glycol vinyl ether, dimethylaminoethyl vinyl ether, diethylaminoethyl vinyl ether, butylaminoethyl vinyl ether, benzyl vinyl ether, or tetrahydrofurfuryl vinyl ether; and vinyl aryl ether such as vinyl phenyl ether, vinyl tolyl ether, vinyl chlorophenyl ether, vinyl-2,4-dichlorophenyl ether, vinyl naphthyl ether, or vinyl anthranyl ether.

Examples of the vinyl esters include vinyl butyrate, vinyl isobutyrate, vinyl trimethyl acetate, vinyl diethyl acetate, vinyl valerate, vinyl caproate, vinyl chloroacetate, vinyl dichloroacetate, vinyl methoxy acetate, vinyl butoxy acetate, vinyl phenyl acetate, vinyl acetoacetate, vinyl lactate, vinyl-β-phenyl butyrate, vinyl benzoate, vinyl salicylate, vinyl chlorobenzoate, vinyl tetrachlorobenzoate, and vinyl naphthoate.

Examples of the styrenes include styrene; alkylstyrene such as methylstyrene, dimethylstyrene, trimethylstyrene, ethylstyrene, diethylstyrene, isopropylstyrene, butylstyrene, hexylstyrene, cyclohexylstyrene, decylstyrene, benzylstyrene, chloromethylstyrene, trifluoromethylstyrene, ethoxymethylstyrene, or acetoxymethylstyrene; alkoxystyrene such as methoxystyrene, 4-methoxy-3-methylstyrene, or dimethoxystyrene; and halostyrene such as chlorostyrene, dichlorostyrene, trichlorostyrene, tetrachlorostyrene, pentachlorostyrene, bromostyrene, dibromostyrene, iodostyrene, fluorostyrene, trifluorostyrene, 2-bromo-4-trifluoromethylstyrene, or 4-fluoro-3-trifluoromethylstyrene.

Examples of the compound having a bifunctional ethylenically unsaturated bond include polyethylene glycol di(meth)acrylate, polypropylene glycol di(meth)acrylate, polyethylene polypropylene glycol di(meth)acrylate, ethylene glycol di(meth)acrylate, propylene glycol di(meth)acrylate, polyethylene polytrimethylolpropane di(meth)acrylate, 2-(meth)acroyloxy-2-hydroxypropylphthalate, 2-(meth)acroyloxyethyl-2-hydroxyethylphthalate, a compound obtained by reacting a glycidyl group-containing compound with α,β-unsaturated carboxylic acid, a urethane monomer, γ-chloro-β-hydroxypropyl-β'-(meth)acryloyloxyethyl-o-phthalate, β-hydroxyethyl-β'-(meth)acryloyloxyethyl-o-phthalate, β-hydroxypropyl-β'-(meth)acryloyloxyethyl-o-phthalate, and isocyanuric acid EO-modified diacrylate.

Examples of the compound obtained by reacting the glycidyl group-containing compound with α,β-unsaturated carboxylic acid include triglycerol di(meth)acrylate. Examples of the urethane monomer include an addition reactant of a (meth)acrylic monomer containing a hydroxyl group at the β-position and isophorone diisocyanate, 2,6-toluene diisocyanate, 2,4-toluene diisocyanate, or 1,6-hexamethylene diisocyanate, EO-modified urethane di(meth)acrylate, and EO/PO-modified urethane di(meth)acrylate.

Examples of the compound having a polyfunctional ethylenically unsaturated bond include tri- or higher functional acrylate such as trimethylolpropane tri(meth)acrylate, pentaerythritol tetra(meth)acrylate, EO-modified pentaerythritol tetra(meth)acrylate, PO-modified pentaerythritol tetra (meth)acrylate, dipentaerythritol penta(meth)acrylate, or dipentaerythritol hexa(meth)acrylate; polyfunctional urethane (meth)acrylate (such as isocyanuric acid EO-modified triacrylate) obtained by reacting a polyisocyanate compound with a hydroxy group-containing (meth)acrylate monomer; and a condensate of polyhydric alcohol and N-methylol (meth)acrylamide.

Photopolymerization Initiator

The photosensitive adhesive contains a photopolymerization initiator in an amount of preferably 0.5% by mass to 5.0% by mass and more preferably 1.0% by mass to 4.0% by mass with respect to the total mass (100% by mass) of the photosensitive adhesive. In a case where the photosensitive adhesive contains such an amount of the photopolymerization initiator, cytotoxicity caused by residual monomers and the photopolymerization initiator of the photosensitive adhesive layer obtained by exposing the photosensitive adhesive so as to be cured can be reduced.

The photopolymerization initiator is appropriately selected from photopolymerization initiators which have been used in the related art according to the kind of the photopolymerizable compound in a range where the purpose of the present invention is not impaired. Examples of suitable photopolymerization initiators in a case of using a photopolymerizable compound having an ethylenically unsaturated bond include 1-hydroxycyclohexyl phenyl ketone, 2-hydroxy-2-methyl-1-phenylpropane-1-one, 1-[4-(2-hydroxyethoxy)phenyl]-2-hydroxy-2-methyl-1-propane-1-one, 1-(4-isopropylphenyl)-2-hydroxy-2-methylpropane-1-one, 1-(4-dodecylphenyl)-2-hydroxy-2-methylpropane-1-one, 2,2-dimethoxy-1,2-diphenylethane-1-one, bis(4-dimethylaminophenyl) ketone, 2-methyl-1-[4-(methylthio)phenyl]-2-morpholinopropane-1-one, 2-benzyl-2-dimethylamino-1-(4-morpholinophenyl)-butane-1-one, ethanone, 1-[9-ethyl-6-(2-methylbenzoyl)-9H-carbazol-3-yl], 1-(o-acetyloxime), 2,4,6-trimethylbenzoyl diphenyl phosphine oxide, 4-benzoyl-4'-methyl dimethyl sulfide, 4-dimethylaminobenzoic acid, methyl 4-dimethylaminobenzoate, ethyl 4-dimethylaminobenzoate, butyl 4-dimethylaminobenzoate, 4-dimethylamino-2-ethylhexyl benzoic acid, 4-dimethylamino-2-isoamyl benzoic acid, benzyl-β-methoxyethyl acetal, benzyl dimethyl ketal, 1-phenyl-1,2-propanedione-2-(o-ethoxycarbonyl) oxime, methyl o-benzoyl benzoate, 2,4-diethylthioxanthone, 2-chlorothioxanthone, 2,4-dimethylthioxanthone, 1-chloro-4-propoxythioxanthone, thioxanthene, 2-chlorothioxanthene, 2,4-diethylthioxanthene, 2-methylthioxanthene, 2-isopropylthioxanthene, 2-ethylanthraquinone, octamethylanthraquinone, 1,2-benzanthraquinone, 2,3-diphenylanthraquinone, azobisisobutyronitrile, benzoyl peroxide, cumene peroxide, 2-mercaptobenzoimidal, 2-mercaptobenzoxazole, 2-mercaptobenzothiazole, 2-(o-chlorophenyl)-4,5-di(m-methoxyphenyl)-imidazolyl dimer, benzophenone, 2-chlorobenzophenone, p,p'-bisdimethylaminobenzophenone, 4,4'-bisdiethylaminobenzophenone, 4,4'-dichlorobenzophenone, 3,3-dimethyl-4-methoxybenzophenone, benzyl, benzoin, benzoin methyl ether, benzoin ethyl ether, benzoin isopropyl ether, benzoin-n-butyl ether, benzoin isobutyl ether, benzoin butyl ether, acetophenone, 2,2-diethoxyacetophenone, p-dimethylacetophenone, p-dimethylaminopropiophenone, dichloroacetophenone, trichloroacetophenone, p-tert-butylacetophenone, p-dimethylaminoacetonone, p-tert-butyltrichloroacetophenone, p-tert-butyldichloroacetophenone, α,α-dichloro-4-phenoxyacetophenone, thioxanthone, 2-methylthioxanthone, 2-isopropylthioxanthone, dibenzosuberone, pentyl-4-dimethylaminobenzoate, 9-phenylacridine, 1,7-bis-(9-acridinyl) heptane, 1,5-bis-(9-acridinyl) pentane, 1,3-bis-(9-acridinyl) propane, p-methoxytriazine, 2,4,6-tris(trichloromethyl)-s-triazine, 2-methyl-4,6-bis(trichloromethyl)-s-triazine, 2-[2-(5-methylfuran-2-yl)ethenyl]-4,6-bis(trichloromethyl)-s-triazine, 2-[2-(furan-2-yl)ethenyl]-4,6-bis(trichloromethyl)-s-triazine, 2-[2-(4-diethylamino-2-methylphenyl)ethenyl]-4,6-bis(trichloromethyl)-s-triazine, 2-[2-(3,4-dimethoxyphenyl)ethenyl]-4,6-bis(trichloromethyl)-s-triazine, 2-(4-methoxyphenyl)-4,6-bis(trichloromethyl)-s-triazine, 2-(4-ethoxystyryl)-4,6-bis(trichloromethyl)-s-triazine, 2-(4-n-butoxyphenyl)-4,6-bis(trichloromethyl)-s-triazine, 2,4-bis-trichloromethyl-6-(3-bromo-4-methoxy)phenyl-s-triazine, 2,4-bis-trichloromethyl-6-(2-bromo-4-methoxy)phenyl-s-triazine, 2,4-bis-trichloromethyl-6-(3-bromo-4-methoxy) styrylphenyl-s-triazine, and 2,4-bis-trichloromethyl-6-(2-bromo-4-methoxy)styrylphenyl-s-triazine. Among these, from the viewpoint that the cytotoxicity of the cell culture chip formed using the photosensitive adhesive is low, a photopolymerization initiator selected from an α-aminoalkylphenone-based photopolymerization initiator and an oxime ester-based photopolymerization initiator is preferable. These photopolymerization initiators can be used alone or in combination of two or more kinds thereof.

Other Components

The photosensitive adhesive may contain additives such as a solvent (for example, propylene glycol-1-methyl ether acetate (PGMEA)), a surfactant, an adhesion improver, a thermal polymerization inhibitor, and an antifoaming agent as necessary, in addition to the photopolymerizable compound and the photopolymerization initiator. As all the above-described additives, known additives of the related art can be used. Examples of the surfactant include an anionic compound, a cationic compound, and a nonionic compound. Examples of the adhesion improver include known silane coupling agents of the related art. Examples of the thermal polymerization inhibitor include hydroquinone and hydroquinone monoethyl ether. Examples of the antifoaming agent include a silicone-based compound and a fluorine-based compound.

<<Photosensitive Shaping Material>>

From the viewpoint that the photosensitive shaping material is used for cell culture, it is preferable that the photosensitive shaping material has low cytotoxicity. Further, a solvent-free material is preferable as the photosensitive shaping material, and it is preferable that the photosensitive shaping material has low autofluorescence and low warpage (also referred to as "low curing shrinkage" or "low elasticity").

Photopolymerizable Compound

The photosensitive shaping material contains a photopolymerizable compound in an amount of preferably 91% by mass to 99.5% by mass and more preferably 92% by mass to 99% by mass with respect to the total mass (100% by mass) of the photosensitive shaping material.

The photosensitive shaping material can be selected from various photopolymerizable compounds which have been used in photosensitive shaping materials in the related art. Examples of the photopolymerizable compound include those exemplified in the section of "•Photopolymerizable compound" of <<Photosensitive Adhesive>> Described Above.

Photopolymerization Initiator

The photosensitive shaping material contains a photopolymerization initiator in an amount of preferably 0.5% by mass to 9.0% by mass and more preferably 1.0% by mass to 8.0% by mass with respect to the total mass (100% by mass) of the photosensitive shaping material. In a case where the photosensitive shaping material contains such an amount of the photopolymerization initiator, cytotoxicity caused by residual monomers and the photopolymerization initiator of the photosensitive shaping material layer obtained by exposing the photosensitive shaping material so as to be cured can be reduced.

Examples of the photopolymerization initiator include those exemplified in the section of "•Photopolymerization initiator" of <<Photosensitive adhesive>> described above.

Hereinafter, the method of producing a cell culture chip of the present embodiment will be described in detail with reference to the accompanying drawings.

Figure 2:
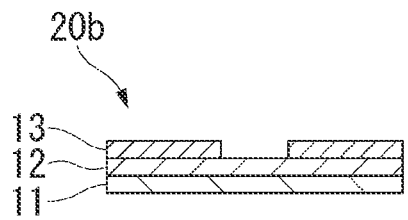
FIG. 2 is a cross-sectional view schematically illustrating a configuration in a step B.

FIG. 1 is a cross-sectional view schematically illustrating the configuration in the step A for explaining an embodiment of the method of producing a cell culture chip. FIG. 2 is a cross-sectional view schematically illustrating the configuration in the step B.

[Step A]

In the present step A, a cell culture flow path substrate 5 including a recessed portion on which one or more cell culture flow paths are formed and a flat portion around the recessed portion, which is a portion bonded to the cell culture flow path top plate is obtained. In the present step A, the cell culture flow path substrate is obtained by performing the following operations (a1) to (a4).

In Regard to Operation (a1):

First, a substrate 1 having transparency is coated with a photosensitive adhesive. Next, the photosensitive adhesive is dried after an optional time so that a photosensitive adhesive layer 2 is formed, thereby obtaining a 3D printing substrate 10 (see [operation (a1)] of FIG. 1).

A method of forming the photosensitive adhesive layer 2 on the substrate 1 having transparency is not particularly limited, and examples thereof include a method of adding a predetermined amount of the photosensitive adhesive dropwise to the substrate 1 having transparency, a method of using a contact transfer type coating device such as a roll coater, a reverse coater, or a bar coater, and a method of using a non-contact type coating device such as a spinner (rotary coating device) or a curtain flow coater.

The thickness of the photosensitive adhesive layer 2 may be, for example, in a range of 5 µm to 50 µm, in a range of 8 µm to 30 µm, or in a range of 10 µm to 25 µm.

The thickness of the substrate 1 having transparency may be, for example, in a range of 50 µm to 250 µm, in a range of 100 µm to 230 µm, or in a range of 150 µm to 200 µm.

The substrate 1 having transparency may include a lubricative layer on at least one surface thereof. In this case, the thickness of the lubricative layer may be, for example, 0.1 µm or less or 50 nm or less. A method of forming the lubricative layer is not particularly limited, and examples thereof include a method of forming a lubricative layer using a so-called in-line coating system, in which original fabric before being stretched in a case of producing the substrate 1 having transparency is coated and stretched, and a lamination method using coextrusion.

In Regard to Operation (a2):

A photosensitive shaping material 3' is film-formed on the 3D printing substrate 10 prepared in the operation (a1) so that a first photosensitive shaping material layer 3a is formed. Next, the first photosensitive shaping material layer 3a is selectively irradiated with ultraviolet rays 8 so that the first photosensitive shaping material layer 3a is selectively cured (see [Operation (a2)] in FIG. 1).

A liquid tank photopolymerization method (optical shaping method) can be used as a method of forming the photosensitive shaping material layer 3a on the 3D printing substrate 10.

As a specific example of the liquid tank photopolymerization method, the 3D printing substrate 10 is placed on a work table 4 that is present in a tank 5a filled with the photosensitive shaping material 3' in a liquid state, and the 3D printing substrate 10 is selectively irradiated with the ultraviolet rays 8 to selectively cure the first photosensitive shaping material layer 3a during the formation of the first photosensitive shaping material layer 3a.

As a method of applying ultraviolet rays, a light source 6 that emits ultraviolet rays, such as a high-pressure mercury lamp, an ultra-high pressure mercury lamp, a xenon lamp, a carbon arc lamp, a HeCd laser, or an Ar laser, is allowed to pass through a modulator or the like as necessary and then pass through a lens or the like, and the photosensitive shaping material layer 3a may be cured so as to have a predetermined thickness while drawing carried out using a digital micromirror device 7 or the like is controlled.

The exposure amount of ultraviolet rays to be applied to the photosensitive shaping material layer 3a is appropriately determined in consideration of the composition of the photosensitive shaping material 3', the film thickness of the photosensitive shaping material layer 3a, and the like. Typically, the exposure amount of ultraviolet rays to be applied to the photosensitive shaping material layer 3a is preferably in a range of 10 mJ/cm$^2$ to 100000 mJ/cm$^2$ and more preferably in a range of 100 mJ/cm$^2$ to 50000 mJ/cm$^2$.

In [Operation (a2)] of FIG. 1, a method in which the light source 6 is present on an upper side and the lamination is made while the work table 4 is pulled down is exemplified, but a method in which the light source 6 is present on a lower side and the lamination is made while the work table 4 is pulled up may be employed.

The thickness of the photosensitive shaping material layer 3a may be, for example, in a range of 0.1 µm to 100 µm, in a range of 1 µm to 80 µm, or in a range of 1 µm to 60 µm.

In a case where the thickness of the photosensitive shaping material layer 3a is in the above-described range, the cell culture chip can have a high resolution.

In regard to operation (a3):

Next, the photosensitive shaping material 3' is further film-formed, the second photosensitive shaping material layer 3b is layered on the selectively cured first photosensitive shaping material layer 3a, the layered second photosensitive shaping material layer 3b is selectively irradiated with ultraviolet rays to selectively cure the layered second photosensitive shaping material layer 3b (see [Operation (a3)] in FIG. 1).

Specifically, the work table 4 where the 3D printing substrate 10 on which the selectively cured first photosensitive shaping material layer 3a is formed is placed is lowered and selectively irradiated with ultraviolet rays 8 to selectively cure the layered second photosensitive shaping material layer 3b during the formation of the second photosensitive shaping material layer 3b.

In Regard to Operation (a4):

Next, the operation (a3) is repeatedly performed a plurality of times so that each photosensitive shaping material layer 3b is cured one by one, the layers are laminated and immersed in a tank 5b containing a developer 9, thereby developing an uncured portion. In this manner, a cell culture flow path substrate 20a including a recessed portion 3d on which one or more cell culture flow paths 3e are formed and a flat portion 3c around the recessed portion 3d, which is a portion bonded to the cell culture flow path top plate is obtained (see [Operation (a4)] in FIG. 1).

In the present embodiment, the recessed portion 3d is sealed by the first adhesive layer while a space which is the cell culture flow path 3e is maintained. The flat portion 3c is directly bonded to the second adhesive layer.

Further, in [Operation (a4)] of FIG. 1, two photosensitive shaping material layers 3a and two photosensitive shaping material layers 3b are formed, but three or more of photosensitive shaping material layers may be formed.

As a method of developing the uncured portion, the 3D printing substrate 10 including the laminated photosensitive shaping material layers 3a and 3b is immersed in a developer to remove the uncured portion.

Examples of the developer include organic solvents such as propylene glycol-1-methyl ether acetate (PGMEA), isopropyl alcohol (IPA), and acetone. After the 3D printing substrate 10 is immersed in a developer, the 3D printing substrate 10 may be further washed with a rinse liquid (for example, an organic solvent or water).

Further, the cell culture flow path substrate 20a after the development may be subjected to a plasma treatment. The cell culture flow path 3e to which cells easily adhere can be formed by performing a plasma treatment on the cell culture flow path substrate 20a. The plasma used for the plasma treatment is not particularly limited, and examples thereof include $O_2$ plasma, $N_2$ plasma, and $CF_4$ plasma.

[Step B]

In the present step B, the first adhesive layer and the second adhesive layer are selectively disposed on the first substrate having transparency to obtain a cell culture flow path top plate.

In the present step B, the first adhesive is film-formed on the first substrate such that the first adhesive layer and the recessed portion face each other. The second adhesive is film-formed on the first substrate such that the second adhesive layer and the flat portion face each other.

The first adhesive contains a polyester-based resin having a glass transition temperature of 5° C. or higher. The second adhesive contains a polyester-based resin having a glass transition temperature of lower than 5° C.

<<First Substrate Having Transparency>>

From the viewpoint of observing cultured cells using a phase contrast microscope or the like, a substrate having transparency is used as the first substrate. Further, in order to enhance the transparency, it is preferable that the substrate does not contain a filler (anti-blocking agent).

Examples of the material of the first substrate include those exemplified in the section of <<Substrate having transparency>> described above.

The first substrate may include a lubricative layer containing a lubricant component on at least one surface thereof. Further, a binder resin component may be blended into the lubricative layer. Examples of the lubricant component and the binder resin component include those exemplified in the section of <<Substrate having transparency>> described above.

<<First Adhesive>>

The first adhesive contains a polyester-based resin having a glass transition temperature (Tg) of 5° C. or higher.

Since the cells are maintained and cultured in a constant temperature environment of approximately 37° C., it is preferable that the first adhesive has low deformability in an environment of 37° C. Further, it is preferable that the first adhesive has adhesiveness to the first substrate, adhesiveness to the cell culture flow path substrate formed in the operations (a2) to (a4), transparency, low self-luminescence, low cytotoxicity, and germicidal detergent resistance.

The first adhesive contains a polyester-based resin having a Tg of 5° C. or higher, preferably a polyester-based resin having a Tg of 10° C. or higher, and more preferably a polyester-based resin having a Tg of 20° C. or higher. Meanwhile, the upper limit of the Tg of the polyester-based resin is preferably 85° C. or lower and more preferably 70° C. or lower.

In a case where the material of the first adhesive is a polyester-based resin having a Tg of 5° C. or higher, the first adhesive has low deformability in an environment of 37° C. and cells can be stably and safely cultured in a constant temperature environment of approximately 37° C.

The first adhesive contains, for example, preferably a polyester-based resin having a Tg of 5° C. to 85° C., more preferably a polyester-based resin having a Tg of 10° C. to 70° C., and still more preferably a polyester-based resin having a Tg of 20° C. to 70° C.

The content of the polyester-based resin having a Tg of 5° C. or higher in the first adhesive is preferably in a range of 5% by mass to 30% by mass and more preferably in a range of 10% by mass to 25% by mass with respect to the total mass (100% by mass) of the first adhesive.

Specifically, as the polyester-based resin having a Tg of 5° C. or higher, for example, "VYLON (registered trademark)" series (manufactured by Toyobo Co., Ltd.) are suitable in terms that a wide variety of resins can be obtained.

Examples of the polyester-based resin having a Tg of 5° C. or higher in "VYLON (registered trademark)" series (manufactured by Toyobo Co., Ltd.) include the followings.

Examples thereof include VYLON 103 (47° C.), VYLON 200 (67° C.), VYLON 220 (53° C.), VYLON 226 (65° C.), VYLON 240 (60° C.), VYLON 245 (60° C.), VYLON 270 (67° C.), VYLON 280 (68° C.), VYLON 290 (72° C.), VYLON 296 (71° C.), VYLON 300 (7° C.), VYLON 600 (47° C.), VYLON 630 (7° C.), VYLON 650 (10° C.), VYLON GK110 (50° C.), VYLON GK130 (15° C.), VYLON GK140 (20° C.), VYLON GK150 (20° C.) VYLON GK190 (11° C.), VYLON GK250 (60° C.), VYLON GK330 (16° C.), VYLON GK360 (56° C.), VYLON GK590 (15° C.), VYLON GK640 (79° C.), VYLON GK680 (10° C.), VYLON GK780 (36° C.), VYLON GK810 (46° C.), VYLON GK880 (84° C.), and VYLON GK890 (17° C.).

Each Tg described above indicates the temperature described in the homepage. Further, the number average molecular weight (Mn) of the polyester-based resin is in a range of $3 \times 10^3$ to $30 \times 10^3$.

In the present specification, the "glass transition temperature (Tg)" indicates the temperature at which the tangents intersect with each other at the inflection point of the measured temperature obtained by differential scanning calorimetry (DSC) under the condition of a temperature rising rate of 20° C./min In the present specification, the "number average molecular weight (Mn)" is acquired in terms of polystyrene according to gel permeation chromatography (GPC).

The polyester-based resin may be crosslinked with a melamine resin or the like. Examples of the melamine resin include "SUMIMAR (registered trademark)" series (manufactured by Sumitomo Chemical Co., Ltd.) and "CYMEL (registered trademark)" series (manufactured by Mitsui Cytec Ltd.).

Further, from the viewpoint of the balance between the workability and the durability, it is preferable that the ratio of the resin and a crosslinking agent is set such that the content of the crosslinking agent (after the reaction) to be blended in the dried first adhesive layer is in a range of 5% by mass to 30% by mass.

The first adhesive may contain a resin other than the polyester-based resin having a Tg of 5° C. or higher, and examples thereof include an acrylic resin having a Tg of 5° C. or higher, a urethane-based resin having a Tg of 5° C. or higher, a polyolefin-based resin having a Tg of 5° C. or higher, a fluorine-based resin having a Tg of 5° C. or higher, and a silicone-based resin having a Tg of 5° C. or higher, mixtures of these resins, and modified resins. Further, the first adhesive may contain additives such as a solvent (for example, cyclohexanone, or propylene glycol-1-methyl ether acetate (PGMEA)), a surfactant, and an antifoaming agent as necessary.

<<Second Adhesive>>

The second adhesive contains a polyester-based resin having a glass transition temperature of lower than 5° C. The second adhesive contains a polyester-based resin having a Tg of lower than 5° C., and the lower limit of the Tg of the polyester-based resin is preferably −30° C. or higher and more preferably −25° C. or higher.

Since the material of the second adhesive is a polyester-based resin having a Tg of lower than 5° C., the adhesive strength between the cell culture flow path substrate and the cell culture flow path top plate is enhanced, and liquid leakage from the flow path while the culture solution at approximately 37° C. is allowed to flow is suppressed.

The second adhesive contains, for example, preferably a polyester-based resin having a Tg of −30° C. or higher and lower than 5° C. and more preferably a polyester-based resin having a Tg of −25° C. or higher and lower than 5° C.

The content of the polyester-based resin having a Tg of lower than 5° C. in the second adhesive is preferably in a range of 5% by mass to 40% by mass and more preferably in a range of 10% by mass to 30% by mass with respect to the total mass (100% by mass) of the second adhesive.

Specifically, as the polyester-based resin having a Tg of lower than 5° C., for example, "VYLON (registered trademark)" series (manufactured by Toyobo Co., Ltd.) are suitable in terms that a wide variety of resins can be obtained.

Examples of the polyester-based resin having a Tg of lower than 5° C. in "VYLON (registered trademark)" series (manufactured by Toyobo Co., Ltd.) include the followings.

Examples thereof include VYLON 500 (4° C.), VYLON 550 (−15° C.), VYLON GK570 (0° C.), VYLON BX1001 (−18° C.), VYLON UR-3200 (−3° C.), VYLON UR-3210 (−3° C.), VYLON UR-6100 (−30° C.), and VYLON UR-8700 (−22° C.).

Each Tg described above indicates the temperature described in the homepage. Further, the number average molecular weight (Mn) of the polyester-based resin is in a range of $19 \times 10^3$ to $40 \times 10^3$.

In the present step B, a first adhesive layer 12 and a second adhesive layer 13 are selectively disposed on a first substrate 11 having transparency to obtain a cell culture flow path top plate 20b.

Specifically, the first substrate 11 is coated with the first adhesive and dried after an optional time to form the first adhesive layer 12 on one surface of the first substrate 11 such that the first adhesive layer 12 and the recessed portion 3d in the cell culture flow path substrate 20a face each other.

Thereafter, the second adhesive layer 13 is selectively disposed on the first adhesive layer 12 using the second adhesive such that the second adhesive layer 13 and the flat portion 3c in the cell culture flow path substrate 20a face each other, thereby obtaining the cell culture flow path top plate 20b (see FIG. 2).

Examples of a method of selectively disposing the second adhesive layer 13 on the first adhesive layer 12 include a method of film-forming the second adhesive on the first adhesive layer 12 and performing patterning such that a region where the first adhesive layer and the recessed portion 3d in the cell culture flow path substrate 20a face each other is a space portion; and a method of film-forming the second adhesive on the substrate to form the second adhesive layer patterned such that the region where the second adhesive layer and the recessed portion 3d in the cell culture flow path substrate 20a face each other is a space portion, positioning the second adhesive layer in the above-described predetermined pattern and the first adhesive layer 12, performing thermocompression-bonding to laminate the second adhesive layer and the first adhesive layer, and peeling the substrate off from this laminate.

Examples of a method of processing the film of the second adhesive into a predetermined pattern include a method of cutting or perforating the film of the second adhesive using a carbon dioxide laser or the like.

The thickness of the first adhesive layer 12 may be, for example, in a range of 5 µm to 50 µm, in a range of 8 µm to 30 µm, or in a range of 10 µm to 25 µm.

The thickness of the second adhesive layer 13 may be, for example, in a range of 1 µm to 40 µm, in a range of 2 µm to 30 µm, or in a range of 5 µm to 20 µm.

The thickness of the first substrate may be, for example, in a range of 50 µm to 250 µm, in a range of 100 µm to 230 µm, or in a range of 150 µm to 200 µm.

The first substrate 11 may include a lubricative layer on at least one surface thereof. In this case, the thickness of the lubricative layer may be, for example, 0.1 µm or less or 50 nm or less.

The method of forming the lubricative layer is not particularly limited, and examples thereof include a method of forming a lubricative layer using a so-called in-line coating system, in which original fabric before being stretched in a case of producing the first substrate 11 is coated and stretched, and a lamination method using coextrusion.

[Step C]

Figure 3:
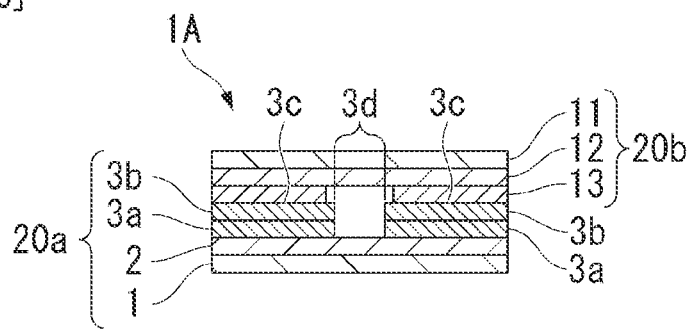
FIG. 3 is a cross-sectional view schematically illustrating a configuration in a step C.

In the present step C, the cell culture flow path substrate 20a obtained in the step A and the cell culture flow path top plate 20b obtained in the step B are positioned with each other and thermocompression-bonded, thereby obtaining a microflow path structure 1A having a hollow structure (see FIG. 3).

Examples of a method of the thermocompression-bonding include a method of thermocompression-bonding the cell culture flow path substrate 20a to the cell culture flow path top plate 20b through a laminate roll or the like in a state in which the cell culture flow path substrate 20a and the cell culture flow path top plate 20b overlap with each other such that the first adhesive layer 12 and the recessed portion 3d face each other and the second adhesive layer 13 and the flat portion 3c face each other.

The temperature condition for compression bonding may be appropriately set according to the kind of the first adhesive. For example, the temperature condition for compression bonding is preferably in a range of 25° C. to 200° C. and more preferably in a range of 50° C. to 160° C.

According to the first embodiment described above, that is, the production method including the step A, the step B, and the step C of performing the operation (a1) to the operation (a4), a cell culture chip, which enables stable production of a fine flow path structure and in which liquid leakage from the flow path is suppressed can be produced.

In the present embodiment, in a case where the cell culture flow path substrate 20a is bonded to the cell culture flow path top plate 20b, the first adhesive layer 12 obtained by using the first adhesive containing a polyester-based resin with a relatively high glass transition temperature (Tg) is disposed on the recessed portion 3d on which the cell culture flow path 3e is formed. Since the Tg of the polyester-based resin constituting the first adhesive layer 12 is high, the heat resistance of the first adhesive layer 12 is enhanced. In this manner, the recessed portion 3d is sealed while the fine flow path structure is stably maintained without blocking the cell culture flow path 3e in the flow direction due to the first adhesive layer 12 during the bonding.

Further, the second adhesive layer 13 obtained by using the second adhesive containing a polyester-based resin having a relatively low glass transition temperature (Tg) is selectively disposed on the flat portion 3c around the recessed portion 3d which is the portion bonded to the cell culture flow path top plate 20b. Since the Tg of the polyester-based resin constituting the second adhesive layer 13 is low, the adhesive strength between the second adhesive layer 13 and the flat portion 3c is increased. In this manner, the adhesiveness between the cell culture flow path substrate 20a and the cell culture flow path top plate 20b is increased.

Due to these effects, in the method of producing a cell culture chip according to the present embodiment, a fine flow path structure can be stably produced, and liquid leakage from the flow path is suppressed even in a case where the cell culture chip has a complicated flow path structure.

In addition, according to the production method of the present embodiment, a cell culture chip which can be mass-produced at a low cost and has a function suitable for cell culture can be produced.

Another Embodiment (1)

The method of producing a cell culture chip according to one embodiment is not limited to the above-described first embodiment. For example, in [Operation (a4)] of FIG. 1, one recessed cell culture flow path 3e is formed, but the present invention is not limited thereto, and a plurality of cell culture flow paths 3e may be formed as illustrated in FIG. 4.

The plurality of cell culture flow paths 3e can be formed by appropriately selecting a site in the photosensitive shaping material layer to be irradiated with ultraviolet rays.

Figure 4:
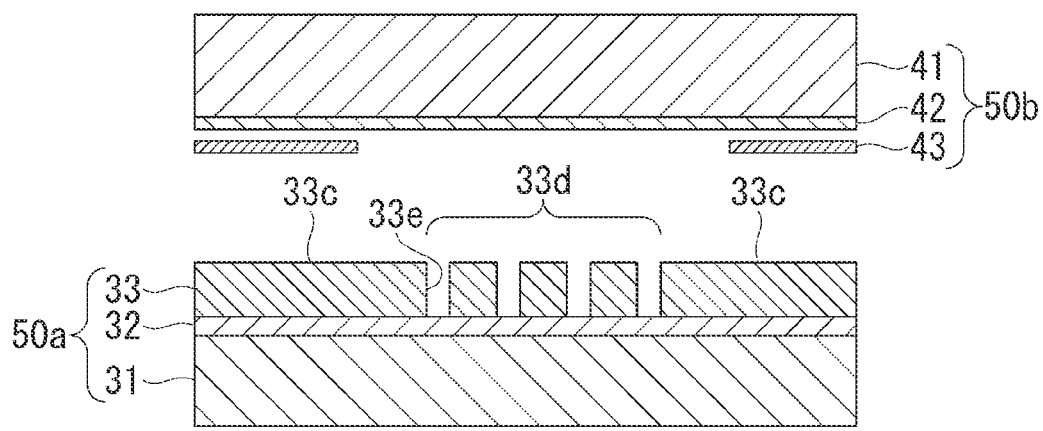
FIG. 4 is a cross-sectional view illustrating another embodiment of a combination of a cell culture flow path substrate and a cell culture flow path top plate.

FIG. 4 is a cross-sectional view illustrating another embodiment of a combination of a cell culture flow path substrate and a cell culture flow path top plate.

In FIG. 4, a cell culture flow path substrate 50a includes a photosensitive shaping material layer 33 on a substrate 31 having transparency through a photosensitive adhesive layer 32. The photosensitive shaping material layer 33 includes a recessed portion 33d on which a plurality of cell culture flow paths 33e are formed; and a flat portion 33c around the recessed portion 33d which is a portion bonded to the cell culture flow path top plate.

The cell culture flow path top plate 50b has a first adhesive layer 42 on one surface of a first substrate 41 having transparency. A second adhesive layer 43 patterned such that the region where the first adhesive layer 42 and the recessed portion 33d in the cell culture flow path substrate 50a face each other is a space portion is provided on the first adhesive layer 42.

The first adhesive layer 42 and the second adhesive layer 43 are respectively selectively disposed such that the first adhesive layer 42 face the recessed portion 33d and the second adhesive layer 43 face the flat portion 33c.

Another Embodiment (2)

Figure 5:
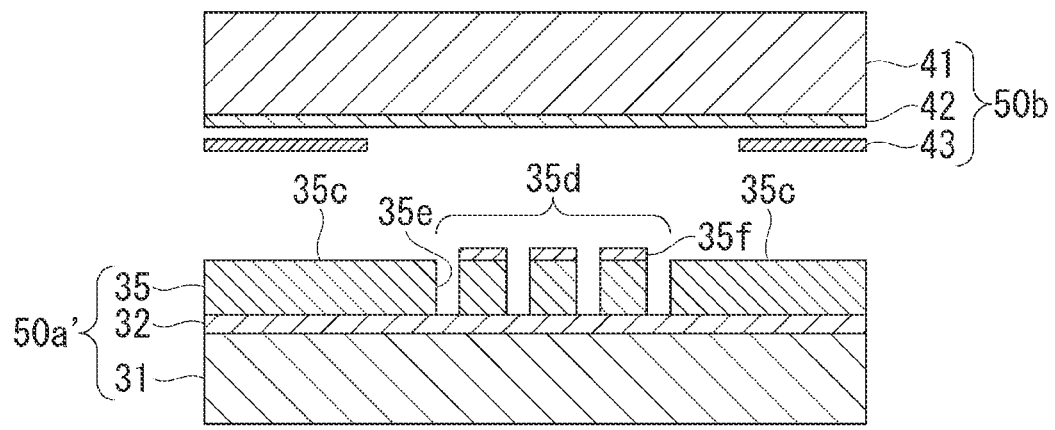
FIG. 5 is a cross-sectional view illustrating still another embodiment of a combination of a cell culture flow path substrate and a cell culture flow path top plate.
Figure 6:
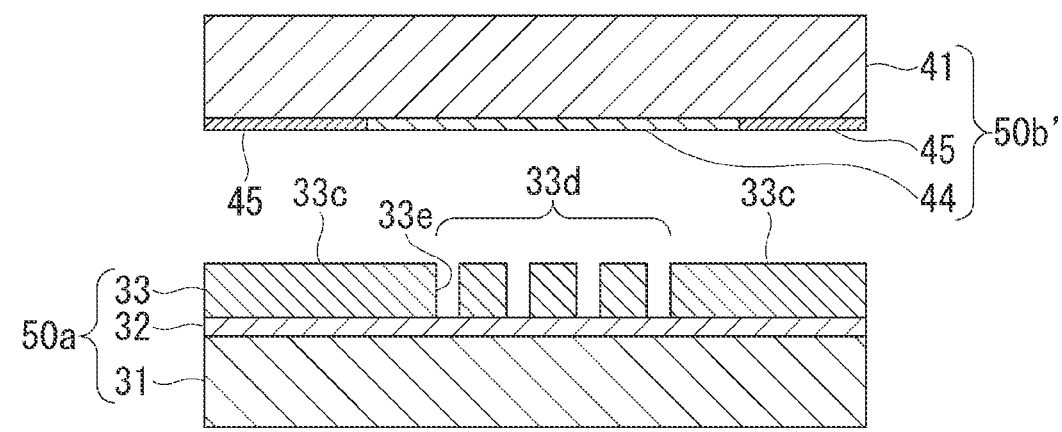
FIG. 6 is a cross-sectional view illustrating even still another embodiment of a combination of a cell culture flow path substrate and a cell culture flow path top plate.

Further, the method of producing a cell culture chip according to one embodiment is not limited to the above-described first embodiment, and for example, a combination of a cell culture flow path substrate and a cell culture flow path top plate as illustrated in FIGS. 5 and 6 may be employed.

In FIG. 5, a cell culture flow path substrate 50a' includes a photosensitive shaping material layer 35 on the substrate 31 having transparency through the photosensitive adhesive layer 32. The photosensitive shaping material layer 35 includes a recessed portion 35d on which a plurality of cell culture flow paths 35e are formed; and a flat portion 35c around the recessed portion 35d which is a portion bonded to the cell culture flow path top plate.

The recessed portion 35d on which the cell culture flow path 35e illustrated in FIG. 5 is formed is provided with a rib 35f protruding more than the height of the flat portion 35c. The height of the rib 35f is, for example, in a range of 10 to 20 μm. A method of forming the rib 35f is not particularly limited, and for example, a lithography method, a printing method, or the like may be used.

The description of the cell culture flow path top plate 50b is the same as the description of the cell culture flow path top plate 50b shown in FIG. 4.

The first adhesive layer 42 and the second adhesive layer 43 are respectively selectively disposed such that the first adhesive layer 42 faces the recessed portion 35d and the second adhesive layer 43 faces the flat portion 35c.

By employing the combination of the cell culture flow path substrate 50a and the cell culture flow path top plate 50b illustrated in FIG. 5, blockage of the cell culture flow path 35e in the flow direction is prevented during the bonding of the cell culture flow path substrate 50a to the cell culture flow path top plate 50b so that the fine flow path structure is stably maintained. Further, since the rib 35f is provided, the first adhesive layer 42 and the upper surface of the recessed portion 35d are easily brought into contact with each other so that the adhesiveness between the cell culture flow path substrate 50a and the cell culture flow path top plate 50b is enhanced.

Due to these effects, in the embodiment in which the combination of the cell culture flow path substrate 50a and the cell culture flow path top plate 50b illustrated in FIG. 5 is employed, a fine flow path structure can be stably produced, and liquid leakage from the flow path is suppressed.

In FIG. 6, the description of the cell culture flow path substrate 50a is the same as the description of the cell culture flow path substrate 50a illustrated in FIG. 4.

A cell culture flow path top plate 50b' includes a first adhesive layer 44 at the central portion of one surface of the first substrate 41 having transparency. Further, a second adhesive layer 45 is provided at a peripheral end portion of one surface of the first substrate 41 having transparency so as to surround the first adhesive layer 44.

The first adhesive layer 44 and the second adhesive layer 45 are respectively selectively disposed such that the first adhesive layer 44 faces the recessed portion 33d and the second adhesive layer 45 faces the flat portion 33c.

As described above, as a method of selectively disposing the first adhesive layer 44 and the second adhesive layer 45 on the same surface, a printing method or the like may be used.

By employing the combination of the cell culture flow path substrate 50a and the cell culture flow path top plate 50b' illustrated in FIG. 6, the adhesive layers do not overlap with each other, and blockage of the cell culture flow path 33e in the flow direction is prevented during the bonding of the cell culture flow path substrate 50a to the cell culture flow path top plate 50b' so that the adhesiveness therebetween can be enhanced.

Another Embodiment (3)

The method of producing a cell culture chip according to one embodiment is not limited to the first embodiment described above, and for example, an embodiment in which the following operation (a5) is further performed after the above-described operations (a1) to (a4) in the step A may be employed.

The operation (a5) is an operation of irradiating the entire surface of the cell culture flow path substrate obtained after the operation (a4) with ultraviolet rays to cure an uncured component.

In the operation (a5), the entire surface of the cell culture flow path substrate 20a obtained in the operation (a4) of the step A is irradiated with ultraviolet rays to cure the uncured component (not illustrated).

Examples of a method of applying ultraviolet rays include those exemplified as the method of applying ultraviolet rays in the section of "In regard to operation (a2)" described above. Typically, the exposure amount of ultraviolet rays to be applied to the cell culture flow path substrate 20a is preferably in a range of 10 mJ/cm$^2$ to 200000 mJ/cm$^2$ and more preferably in a range of 100 mJ/cm$^2$ to 100000 mJ/cm$^2$.

By employing the embodiment in which the operation (a5) is further performed after the operations (a1) to (a4) in the step A, uncured photopolymerizable compounds contained in the photosensitive shaping material layers 3a and 3b and the photosensitive adhesive layer 2 can be sufficiently cured.

Another Embodiment (4)

Further, the method of producing a cell culture chip according to one embodiment is not limited to the first embodiment described above, and for example, an embodiment in which the above-described operation (a5) is performed after the above-described operations (a1) to (a4), and the following operation (a6) is further performed in the step A may be employed.

The operation (a6) is an operation of washing the cell culture flow path substrate obtained after the operation (a5) using an organic solvent to remove the uncured component.

In the operation (a6), the cell culture flow path substrate 20a cured by applying ultraviolet rays to the entire surface thereof is washed with an organic solvent to remove the uncured component (not illustrated).

Examples of the organic solvent to be used include a non-polar solvent such as hexane, benzene, toluene, diethyl ether, chloroform, ethyl acetate, methylene chloride, PGMEA, or propylene glycol monomethyl ether; and a polar solvent such as tetrahydrofuran, acetone, acetonitrile, N,N-dimethylformamide, dimethylsulfoxide, acetic acid, 1-butanol, 1-propanol, 2-propanol, ethanol, methanol, formic acid, or water. These may be used alone or in combination of two or more kinds thereof.

As a washing method using an organic solvent, for example, it is preferable that the cell culture flow path substrate 20a is initially washed with a non-polar solvent and then washed by gradually replacing the non-polar solvent with a polar solvent. Specific examples thereof include a method of washing the cell culture flow path substrate 20a with PGMEA, propylene glycol monomethyl ether, and ethanol in order and drying the cell culture flow path substrate 20a.

By employing the embodiment in which the operation (a5) is performed after the operations (a1) to (a4) and the operation (a6) is further performed in the step A, the uncured photopolymerizable compound remaining in the cell culture flow path can be sufficiently removed.

Another Embodiment (5)

In the first embodiment described above, a method in which a 3D printer is applied as a shaping method is employed, but the present invention is not limited thereto, and a shaping method other than the method of using a 3D printer may be used. Examples thereof include photolithography, in-mold transfer, injection molding, and processing through machining.

Further, the cell culture chip produced by the production method according to the present embodiment includes a support on a lower portion thereof (for example, a surface of the cell culture flow path substrate on a side opposite to the photosensitive adhesive layer of the cell culture flow path substrate) through a third adhesive layer. With such an embodiment, the strength of the cell culture chip can be maintained to be high.

<<Support>>

From the viewpoint of observing cultured cells using a phase contrast microscope or the like, it is preferable that the support has transparency.

Examples of the material of the support include glass, polyethylene terephthalate, polycarbonate, a cycloolefin polymer, polydimethylsiloxane, polystyrene, and polyacrylate.

<<Third Adhesive>>

From the viewpoint of observing cultured cells using a phase contrast microscope or the like, it is preferable that the third adhesive has transparency. Further, it is preferable that the third adhesive has adhesiveness to both the substrate 1 having transparency and the support.

Examples of the third adhesive include those exemplified in the section of <<First adhesive>> described above.

EXAMPLES

Hereinafter, the present invention will be described in more detail with reference to examples, but the present invention is not limited to these examples.

[Production Example 1] Production of Cell Culture Chip

Figure 7:
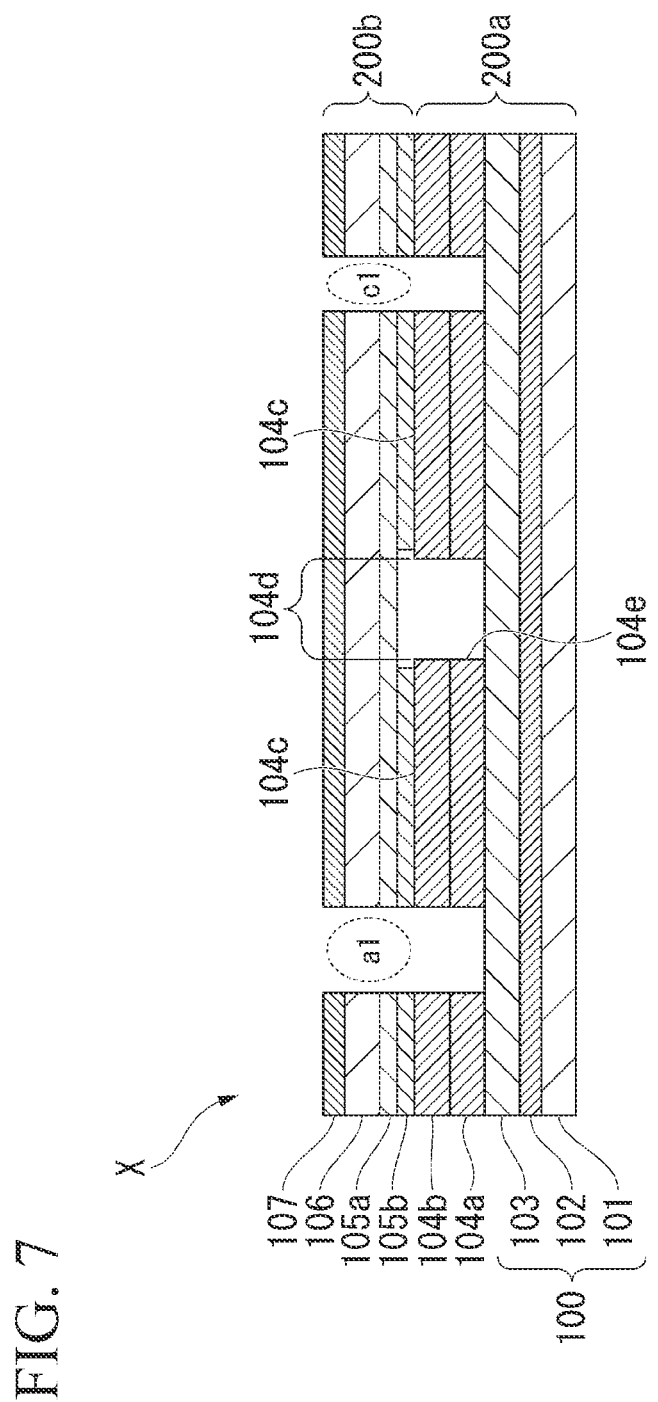
FIG. 7 is a cross-sectional view schematically illustrating a configuration of a microflow path structure (X) having a hollow structure in Production Example 1.

As a microflow path chip for a cell assay, a cell culture chip including a microflow path structure (X) having a hollow structure illustrated in FIG. 7 was produced in the following manner.

1. Preparation of Cell Culture Flow Path Substrate: Step A (1-1) Preparation of First Photosensitive Adhesive The raw materials listed in Table 1 below were sufficiently stirred to obtain a uniform solution, thereby obtaining a first photosensitive adhesive.

TABLE 1

| Name of raw material | Parts by mass |
|---|---|
| ARONIX M313 (manufactured by Toagosei Co., Ltd.) | 100 |
| IRGACURE 184 (manufactured by BASF SE) | 3 |
| Propylene glycol monomethyl ether acetate (PGMEA) | 100 |

(1-2) Preparation of 3D Printing Substrate

Next, a surface (an easy-adhesion treated surface) of a lubricative layer 102 of COSMOSHINE A4100 (manufactured by Toyobo Co., Ltd., polyethylene terephthalate substrate 101) having a film thickness of 188 µm was coated with the first photosensitive adhesive obtained in the preparation (1-1) such that the film thickness after the film had been dried reached 15 µm to form a photosensitive adhesive layer 103, thereby obtaining a 3D printing substrate 100.

(1-3) Preparation of photosensitive shaping material

The raw materials listed in Table 2 below were sufficiently stirred to form a uniform solution, thereby obtaining a photosensitive shaping material.

TABLE 2

| Name of raw material | Parts by mass |
| --- | --- |
| VISCOAT #360 (manufactured by Osaka Organic Chemical Industry Ltd.) | 50 |
| EBECRYL 8802 (manufactured by Daicel-Allnex Ltd.) | 50 |
| KAYACURE DETX-S (manufactured by Nippon Kayaku Co., Ltd.) | 3 |
| KAYACURE EPA (manufactured by Nippon Kayaku Co., Ltd.) | 3 |

(1-4) Preparation of Cell Culture Flow Path Substrate

Next, the 3D printing substrate 100 was coated with the photosensitive shaping material obtained in the preparation (1-3) such that the thickness of one layer reached 20 to 50 µm to form photosensitive shaping material layers 104a and 104b. Thereafter, a digital micromirror device (DMD) was used to selectively project ultraviolet rays having a center wavelength of 370 µm to cure the photosensitive shaping material.

Further, the photosensitive shaping material was multilayered, cured, developed with acetone for 3 minutes, and air-blown using the same method, thereby obtaining a structure including a fine recessed cell culture flow path 104e (recessed portion 104d) and a flat portion 104c around the recessed portion 104d.

Thereafter, the entire structure was irradiated with ultraviolet rays using a high-pressure mercury lamp, washed with PGMEA, propylene glycol monomethyl ether, and ethanol in order, and dried, thereby obtaining a cell culture flow path substrate 200a.

2. Preparation of Cell Culture Flow Path Top Plate: Step B (2-1) Preparation of First Adhesive The raw materials listed in Table 3 below were sufficiently stirred to obtain a uniform solution, thereby obtaining a first adhesive.

TABLE 3

| Name of raw material | Parts by mass |
| --- | --- |
| VYLON GK780 (manufactured by Toyobo Co. Ltd.) (Tg: 36° C.) | 20 |
| Cyclohexanone | 100 |

(2-2) Preparation of Cell Culture Flow Path Top Plate

Next, an untreated surface (a surface on a side opposite to a lubricative layer 107) of COSMOSHINE A4100 (manufactured by Toyobo Co., Ltd., polyethylene terephthalate substrate 106) (first substrate) having a film thickness of 188 µm was coated with the first adhesive obtained in the preparation (2-1) such that the film thickness after the film had been dried reached 20 µm, thereby obtaining a first adhesive layer 105a.

(2-3) Preparation of Second Adhesive

The raw materials listed in Table 4 below were sufficiently stirred to form a uniform solution, thereby obtaining a second adhesive.

TABLE 4

| Name of raw material | Parts by mass |
| --- | --- |
| VYLON 550 (manufactured by Toyobo Co. Ltd.) (Tg: 4° C.) | 20 |
| Cyclohexanone | 80 |

Next, a release-treated surface of Purex A53 (manufactured by Teijin Ltd., third substrate) having a film thickness of 50 µm was coated with the second adhesive obtained in the preparation (2-3) such that the film thickness after the film had been dried reached 10 µm, thereby obtaining a second adhesive layer 105b.

The second adhesive layer 105b was cut into a pattern in which the fine recessed cell culture flow path 104e (recessed portion 104d) was framed using a carbon dioxide laser.

The second adhesive layer 105b cut into a predetermined pattern and the first adhesive layer 105a obtained in the preparation (2-2) were positioned and thermocompression-bonded through a laminate roll heated to 80° C., thereby obtaining a laminate. Here, the first adhesive layer 105a and the second adhesive layer 105b were respectively selectively disposed such that the first adhesive layer 105a faced the recessed portion 104d and the second adhesive layer 105b faced the flat portion 104c. Thereafter, the third substrate was peeled off from the laminate, holes (a1 (3 mm) and c1 (1.5 mm) in FIG. 7) which were inlets were made using a carbon dioxide laser, immersed in ethanol, and dried, thereby obtaining a cell culture flow path top plate 200b.

3. Bonding of Cell Culture Flow Path Substrate to Cell Culture Flow Path Top Plate: Step C Next, double-sided tape having a thickness of 50 µm serving as a temporary fixing agent was attached to the cell culture flow path top plate 200b, the holes (a1 (3 mm) and c1 (1.5 mm) in FIG. 7) were positioned using a microscope such that the holes were able to adhere to a predetermined position of the cell culture flow path substrate 200a, and the surface coated with the first adhesive layer and the second adhesive layer of the cell culture flow path top plate 200b and the cell culture flow path substrate 200a were temporarily fixed to each other.

Thereafter, the cell culture flow path substrate 200a was thermocompression-bonded to the cell culture flow path top plate 200b through a laminate roll heated to 80° C. Here, it was confirmed that the recessed portion was sealed while the fine flow path structure was stably maintained without blocking the cell culture flow path 104e in the flow direction.

A cell culture chip including the microflow path structure (X) having a hollow structure was obtained by performing the series of the step A, the step B, and the step C described above.

<Evaluation of Liquid Leakage from Flow Path>

Dye-dissolved water was circulated to the cell culture chip including the microflow path structure (X) having a hollow structure, which had been produced by the production method of Production Example 1 described above.

Method of preparing dye-dissolved water: using 0.5% trypan blue stain solution (manufactured by Nacalai Tesque Inc.)

Conditions for circulating dye-dissolved water: temperature of 37° C., pump pressure (inflow pressure) of 5 kPa, sending of liquid for 24 hours As a result of circulating the dye-dissolved water to the cell culture chip, it was confirmed that leakage of the dye-dissolved water did not occur.

Therefore, according to the production method to which the present invention is applied, it was found that a cell culture chip which enables stable production of a fine flow path structure and in which liquid leakage from the flow path is suppressed can be produced.

While preferred embodiments of the invention have been described and illustrated above, it should be understood that these are exemplary of the invention and are not to be considered as limiting. Additions, omissions, substitutions, and other modifications can be made without departing from the scope of the invention. Accordingly, the invention is not to be considered as being limited by the foregoing description and is only limited by the scope of the appended claims.

EXPLANATION OF REFERENCES

1: substrate
1A: microflow path structure
2: photosensitive adhesive layer
3': photosensitive shaping material
3a: first photosensitive shaping material layer
3b: second photosensitive shaping material layer
3c: flat portion
3d: recessed portion
3e: cell culture flow path
4: work table
5a: tank
5b: tank
6: light source
7: digital micromirror device
8: ultraviolet rays
9: developer
10: 3D printing substrate
11: first substrate
12: first adhesive layer
13: second adhesive layer
20a: cell culture flow path substrate
20b: cell culture flow path top plate
31: substrate
32: photosensitive adhesive layer
33: photosensitive shaping material layer
33c: flat portion
33d: recessed portion
33e: cell culture flow path
35e: cell culture flow path
41: first substrate
42: first adhesive layer
43: second adhesive layer
44: first adhesive layer
45: second adhesive layer
50a: cell culture flow path substrate
50a': cell culture flow path substrate
50b: cell culture flow path top plate
50b': cell culture flow path top plate
100: 3D printing substrate
101: polyethylene terephthalate substrate
102: lubricative layer
103: photosensitive adhesive layer
104a: photosensitive shaping material layer
104b: photosensitive shaping material layer
104c: flat portion
104d: recessed portion
104e: cell culture flow path
105a: first adhesive layer
105b: second adhesive layer
106: polyethylene terephthalate substrate
107: lubricative layer
200a: cell culture flow path substrate
200b: cell culture flow path top plate
X: microflow path structure

What is claimed is:

1. A method of producing a cell culture, the method comprising:
   a step A of obtaining a cell culture flow path substrate including a recessed portion on which one or more cell culture flow paths are formed and a flat portion around the recessed portion, the flat portion being a portion which is bonded to a cell culture flow path top plate;
   a step B of selectively disposing a first adhesive layer and a second adhesive layer on a first substrate having transparency to obtain the cell culture flow path top plate; and
   a step C of thermocompression-bonding the cell culture flow path substrate to the cell culture flow path top plate to obtain a microflow path structure having a hollow structure to produce the cell culture chip including the microflow path structure in which the cell culture flow path substrate on which the cell culture flow path is formed is bonded to the cell culture flow path top plate through the first and second adhesive layers;
   wherein in the step B, the first adhesive layer is disposed in an area which faces the recessed portion when the cell culture flow path top plate is bonded to the cell culture flow path substrate,
   the second adhesive layer is disposed in an area which faces the flat portion face when the cell culture flow path top plate is bonded to the cell culture flow path substrate,
   the first adhesive layer is formed using a first adhesive containing a polyester-based resin having a glass transition temperature of 5° C. or higher, and
   the second adhesive layer is formed using a second adhesive containing a polyester-based resin having a glass transition temperature of lower than 5° C.

2. The method of producing the cell culture chip according to claim 1, wherein in the step A, the cell culture flow path substrate is obtained by performing operations (a1) to (a4), the operation (a1) of forming a photosensitive adhesive layer by coating the substrate having transparency with a photosensitive adhesive to obtain a 3D printing substrate;
   the operation (a2) of selectively irradiating a photosensitive shaping material layer obtained by film-forming a photosensitive shaping material on the 3D printing substrate with ultraviolet rays to selectively cure the photosensitive shaping material layer;
   the operation (a3) of further film-forming a photosensitive shaping material such that a photosensitive shaping material layer is layered on the selectively cured photosensitive shaping material layer and selectively irradiating the layered photosensitive shaping material layer with ultraviolet rays to selectively cure the layered photosensitive shaping material layer; and
   the operation (a4) of repeatedly performing the operation (a3) a plurality of times and subsequently developing an uncured portion, thereby obtaining the cell culture flow path substrate having the recessed portion and the flat portion.

3. The method of producing the cell culture chip according to claim 2,
   wherein in the step A, an operation (a5) is further performed after the operations (a1) to (a4), the operation (a5) of irradiating an entire surface of the cell culture flow path substrate obtained after the operation (a4) with ultraviolet rays to cure an uncured component.

4. The method of producing the cell culture chip according to claim 3,
wherein in the step A, an operation (a6) is further performed after the operation (a5),
the operation (a6) of washing the cell culture flow path substrate obtained after the operation (a5) with an organic solvent to remove the uncured component.

5. The method of producing the cell culture chip according to claim 4,
wherein in the operation (a6), the cell culture flow path substrate is washed by gradually changing a non-polar solvent to a polar solvent.

* * * * *